United States Patent [19]

Josowicz et al.

[11] Patent Number: 4,959,130
[45] Date of Patent: Sep. 25, 1990

[54] ULTRAMICROELECTRODE, PROCESS FOR MAKING SAME AND ITS APPLICATION

[76] Inventors: Mira Josowicz, Robert Koch Str. 20; Karin Potje-Kamloth, Rathaus-Str. 2, both of 8012 Ottobrunn, Fed. Rep. of Germany

[21] Appl. No.: 353,076
[22] Filed: May 15, 1989
[30] Foreign Application Priority Data
May 13, 1988 [DE] Fed. Rep. of Germany ....... 3816458
[51] Int. Cl.⁵ .................. G01N 27/30; G01N 27/333; C25D 9/02
[52] U.S. Cl. ...................... 204/32.1; 128/635; 128/639; 204/35.1; 204/37.1; 204/38.4; 204/38.5; 204/40; 204/400; 204/416; 204/418; 428/457; 428/461; 428/626
[58] Field of Search ............ 204/56.1, 59 R, 400, 204/32.1, 35.1, 37.1, 38.4, 40, 416, 418; 128/635, 639; 428/457, 626, 461

[56] References Cited
U.S. PATENT DOCUMENTS

| | | | |
|---|---|---|---|
| 3,335,075 | 8/1967 | Borman | 204/59 R |
| 3,455,736 | 7/1969 | Davis et al. | 428/457 X |
| 3,719,576 | 3/1973 | Macur | 204/415 X |
| 4,132,608 | 1/1979 | Chandross et al. | 204/27 |
| 4,334,054 | 6/1982 | DuBois et al. | 528/210 |
| 4,389,516 | 6/1983 | Sugio et al. | 525/534 |

FOREIGN PATENT DOCUMENTS 59-723 4/1984 Japan.
2059994 4/1981 United Kingdom.

*Primary Examiner*—G. L. Kaplan
*Attorney, Agent, or Firm*—Michael J. Striker

[57] ABSTRACT

The ultramicroelectrode comprises a wire or filament of noble metal and/or carbon on which an insulating layer is provided. The insulating layer is made from a crosslinked alkenyl-substituted poly(1,4-phenylene) ether, poly(1,4-phenylene) thioether or poly(1,4-aniline). This ultramicroelectrode can be used as a disk, cylindrical, bipolar or shielded electrode and may be used as a stimulating electrode, amperometric or potentiometric microsensor or as an electrode for analytical measurement, e.g. for inverse voltammetry.

33 Claims, 3 Drawing Sheets

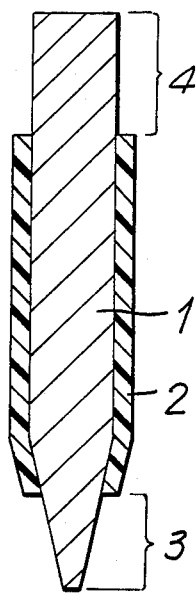
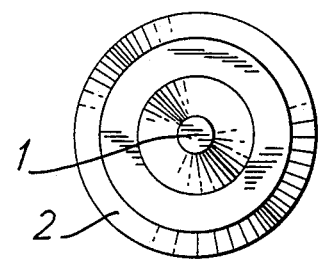
FIG. 2A
FIG. 2B

ULTRAMICROELECTRODE, PROCESS FOR MAKING SAME AND ITS APPLICATION

BACKGROUND OF THE INVENTION

My invention relates to an electrode, particularly an ultramicroelectrode, a process for its manufacture and its use or applications.

An ultramicroelectrode with a conductor made of noble metal wire or carbon wire with an insulating layer located on it is known.

Ultramicroelectrodes are made from very thin electric conductors in the form of filaments or wires with a diameter of a few micrometers and an insulating layer located on it. It is required of these electrodes that they be useable in a wide range of solvents, simple to build, have exact measured dimensions and can produce reproducible results.

The insulating layer of the ultramicroelectrode used currently is made of glass or an epoxy resin. Such microelectrodes are described in the following literature references:

R. W. Wightman and D. O. Wipt, Electroanalytical Chemistry, Vol. 15, pp. 44 to 51, New York, Marcel Dekker-Verlag(1970), Martin Fleischmann, Stanely Pons, Debra R. Rolison and Parbury P. Schmidt: Ultramicroelectrodes, Kapitel 3, pp. 66 to 106, Datatech Systems, Inc., Science Publishers, (1987); D. W. Hill, B. W. Watson, IEE Medical Electronics Monograph 7-12, I. Microelectrodes and Input Amplifiers, pp. 1 to 26, Peter Peregrinus Ltd. (1974). Conventional ultramicroelectrodes are made in the following way: One draws a glass tube into a capillary and in the capillary so drawn introduces a wire or a filament made of noble metal and/or carbon. Then the wire is heat sealed in the glass tube. The thickness of the insulating layer made of glass or epoxy resin is approximately about 1 to 2 mm. Building a uniform layer thickness over the entire electrode length is difficult.

Ultramicroelectrodes with glass insulation are very fragile, since hair-line fractures occur in glass because of thermal stress caused by the difference in the thermal expansion coefficient of glass and the filament material. The hair-line fractures are the basis for a comparatively strong increase in the electrode surface area, for nonlinear diffusion and edge effects. Further the poor adhesion of the encapsulating or encasing materials on the wire or the filament both with glass and also with epoxy resin leads to forcing of fluid under the insulating layer. Also epoxy resins have a poor stability relative to organic solvents, since the components of the resin can be dissolved away. This leads to degradation or altering the epoxy resin. All these effects lead to an increase of the residual current and thus to an increase of the double layer capacitance of the insulating material. Consequently the signal/noise ratio is very unsatisfactory which also affects the response time and the reproducibility of the measurement. Further such ultramicroelectrodes are made by hand, which is connected with high wastage, poor reproducibility and reduced production rate.

SUMMARY OF THE INVENTION

Accordingly, it is an object of my invention to provide a stable commercial electrode, particularly an ultramicroelectrode, with an insulating layer resisting chemical and mechanical influences and with a reduced double layer capacitance which allows a trouble-free analysis of the measurement signals, even for a very rapidly received measured signal. These electrodes can be made with a higher productivity, reproducibility and improved uniformity of the layer formed. The insulating layer can be deposited uniformly independently of the dimensions of the electrical conductors, has no tears and has outstanding adhesion properties.

In keeping with this object and with others which will become apparent hereinafter, the insulating layer is made from alkenyl-substituted poly(1,4-phenylene) ether, poly(1,4-phenylene) thioether or poly(1,4-aniline), whose phenyl groups are cross-linked by alkylene groups in an ortho-position with two to ten carbon atoms.

Several embodiments of our invention are possible. The thickness of the insulating layer amounts to 1.0 to 3.0 micrometers and the wire has a diameter of 0.1 to 15 micrometers. The electrode may be shaped like a disk on one end, which is free of insulating material. Advantageously both ends of the electrode may be free of insulating material.

In one embodiment of our ultramicroelectrode a metal electrode may be put on the surface of an insulating layer and then an insulating layer may be applied again to the metal electrode.

On one end portion or on both end portions of the microelectrode, which are free of the insulating layer, metal is advantageously applied.

Advantageously a portion of the electrode free of an insulating layer is provided with an ion selective layer. The ion selective layer contains as a matrix a copolymer of a phenol-, thiophenol- and/or analine-containing monomer with an unsaturated group in an ortho-position with a noncross-linkable OH—, $NH_2$— or SH-containing aromatic comonomer, which has a saturated aliphatic group in an ortho-position with one to 10 carbon atoms.

Also in keeping with the above object and with others which will become apparent hereinafter, our process for making the above ultramicroelectrode comprises the step of depositing a polymer layer anodically on a wire or filament made of noble metal and/or carbon by electrochemical polymerization of phenol-, thiophenol- and/or aniline-containing monomer, which contains an unsaturated aliphatic group with two to ten carbon atoms in an ortho-position, made from an electrolytic bath having an alkaline medium, especially a primary amine with an aliphatic group or an aqueous ammoniacal solution or a mixture of both and an adhesion promoting agent.

The cross-linking of the polymer layer can occur by heating or by irradiating. The wire or the filament may be advantageously cleaned prior to the chemical and/or electrochemical deposition to remove a passive layer. After the electrochemical deposition step for the polymer layer it is dissolved again chemically on an end region. Prior to the electrochemical deposition an end region or both end regions of the electrode is metallized. The tip of the electrode is mechanically freed of insulator after the cross-linking of the polymer layer, so that the wire and/or the filament is exposed. After electrochemical application of the polymer layer and subsequent cross-linking the insulating layer formed from the polymer layer may be metallized either with physical and/or chemical and/or electrochemical processes.

Advantageously the insulating layer, which is removed less than 2 mm from the electrode active end region of the electrode, is masked prior to any metallizing undertaken or is freed or exposed chemically or electrochemically after metallizing by metal.

An ion selective layer is applied to an end portion of the electrode free of insulating material. As matrix for the ion selective layer a copolymer layer made of phenol-, thiophenol- and/or analine monomer, which has an unsaturated aliphatic group in an ortho-position, is formed with at least one noncross-linkable OH—, $NH_2$— or SH-containing aromatic comonomer by electrochemical deposition and subsequent cross-linking and the ion-selective components are embedded during the electrochemical deposition or after the cross-linking of the copolymer layer. The noncross-linkable comonomer is used in a proportion of at least 40 Mol % of the total Monomer present.

When the insulating layer is made from a cross-linked substituted poly(1,4-phenylene) ether, poly(1,4-phenylene) thioether or poly(1,4-aniline), a high breakdown voltage is attained whereby capacitive coupling of the insulating wall is kept small. Thus when measured signals are received quickly the signal noise and/or the leakage current are continuously suppressed. By the electrochemical application of an insulating layer a very thin and uniform layer thickness on the filament or the wire is attained, whereby an automatic manufacture with increased productivity and good reproducibility is possible.

The use of poly(1,4-phenylene) ether as a corrosion protective layer is described in the literature reference, J. Electochem. Soc.: Electrochemical Science and Technology, pp. 2276 to 2281(1981). Such corrosion protective layers with a thickness of at least 10 micrometers have good physical properties, particularly corrosion resistance. It has been reported that layers with a thickness of only 1 to 2 micrometers show neither improved metal protection properties nor advantages in hardening and/or cross-linking. Because of these disadvantages it could not be expected that such poly(1,4-phenylene) ether layers would be suitable as insulating materials for electrodes when reduced layer thicknesses were used.

BRIEF DESCRIPTION OF THE DRAWING

The objects, features and advantages of my invention will be made more apparent from the following detailed description, reference being made to the accompanying drawing in which:

FIG. 2A is a longitudinal cross sectional view of another embodiment of a coaxially tapered ultramicroelectrode, FIG. 2B is an end-on plan view of the embodiment of FIG. 2A.

DETAILED DESCRIPTION OF THE INVENTION

Figure 1A:
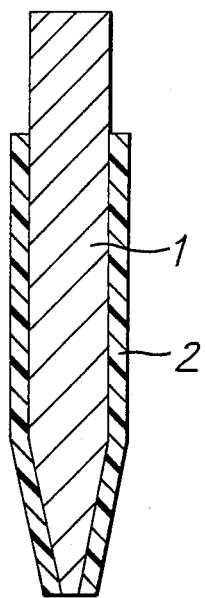
FIG. 1A is a longitudinal cross sectional view of a coaxially tapered ultramicroelectrode.
Figure 1B:
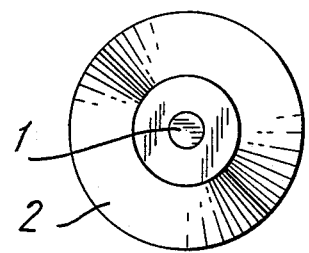
FIG. 1B is an end-on plan view of the ultramicroelectrode.

An embodiment of the electrode is shown in FIGS. 1A and 1B. FIG. 1A shows a longitudinal view of a conically tapered ultramicroelectrode, while FIG. 1B shows an end-on plan view of the electrode. The reference number 1 indicates a noble metal electrode or a carbon filament and the reference number 2 the insulating layer. The ultramicroelectrode is a disk-ultramicroelectrode.

An additional embodiment of the ultramicroelectrode is shown in FIGS. 2A and B in longitudinal and end-on views. The ultramicroelectrode is shown as a cylindrical electrode. The tip and the upper end portion of the electrodes are free of insulating material.

The electrode shown in FIG. 3 is a bipolar ultramicroelectrode. The reference number 1 indicates a noble metal wire or a carbon filament on which the insulating layer 2 is applied. The reference number 12 indicates a metallic layer, which is insulated separately from the conductive layer 6 by epoxy 5 for additional measurement signal leakage. The reference number 14 indicates a glass capillary, which is used as a retaining mean or holder. The lower portion of the electrode 7 is free of metal.

Figure 3B:
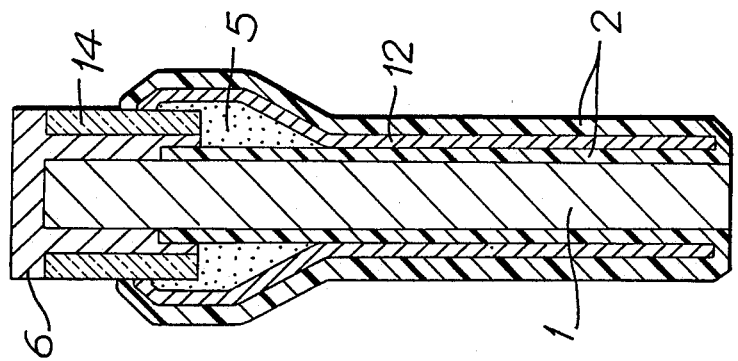
FIG. 3B is another longitudinal cross sectional view of another additional embodiment of an ultramicroelectrode.

An additional embodiment of the electrode is shown in longitudinal cross section in FIG. 3B. The electrode shown is a shielded ultramicroelectrode. The reference numbers 1 to 6 have been used for the same parts as in the previous embodiments.

In the insulating layer according to our invention the substituted phenyl groups are cross-linked by alkylene groups in ortho- or meta-positions having 2 to ten carbon atoms. Advantageously the alkylene groups have a length of from 2 to 5 carbon atoms.

The insulating layers are made in an electrolytic bath on wire or filament by electrochemical polymerization of phenol-, thiophenol- or aniline-containing monomers and their combinations. At least one polymer layer is formed with a linear structure. A linear polymer formed advantageously in an electrochemical deposition has the following structure:

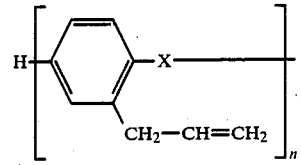

where $X = -O-$, $-S-$ or $-NH-$.

The monomer used must be blocked in the ortho-position, so that a linear polymer structure is formed. Advantageously the phenyl group of the monomer in the ortho-position has an aliphatic group with up to 10 carbon atoms, advantageously up to 5 carbon atoms. This aliphatic group is advantageously unsaturated. A suitable unsaturated aliphatic residue has 2 to 10, advantageously 2 to 5 carbon atoms, and is advantageously a vinyl or allyl group. Advantageously the monomers may be 2-allyl phenol, 2-allyl thiophenol and 2-allyl aniline and/or appropriate vinyl compounds.

The electrochemical deposition occurs advantageously in aqueous media at the anode. Advantageously a water-alcohol mixture is used in which the mixture ratio is 1:10 to 10:1 by volume, advantageously 1:5 to 5:1. A reduced aliphatic alcohol is advantageous. The electrolyte solution contains an amine besides the monomer or an aqueous ammoniacal solution or a mixture of both to suppress the passivity of the electrode surfaces. Advantageously the amine is a primary amine with an aliphatic group. The aliphatic group is advantageously an alkyl group with 1 to 10 carbon atoms, which can be unsaturated. Advantageously amines such as allyl amine and propyl amine may be used.

Advantageously the electrolyte solution contains an adhesion promoting agent which promotes the adherence to the electrode surface. Suitable adhesion promoting agents are ethylene glycol monobutyl ether or butoxy methanol. The adhesion promoting agent is used in a proportion of 1 to 10% by volume relative to the electrolyte solution. The electrochemical deposition occurs at 20° to 50° C., advantageously at room temperature and at constant potential advantageously 2 to 8 volts, especially 4 to 6 volts.

After the electrochemical deposition of the polymer layer on the wire or on the filament occurs a cross-linking of the unsaturated groups present occurs by heating or irradiating. Advantageously a thermal treatment, i.e. a heating, occurs at 120° to 200° C., especially at 150° C. A suitable temperature may easily be determined with the help of suitable simple experiments with a given polymer layer. An irradiation treatment with UV-radiation is also possible.

So that a good adherence of the insulated layer and the filament and/or the filament is guaranteed, whether the wire or the filament is free of its passive layer prior to the electrochemical deposition must be carefully considered. For this purpose the wire or the filament should be cleaned chemically and/or electrochemically to remove the passive layer. A suitable process consists of an electrochemical etching with a solution of ethylene diamine tetraacetate, $NH_4OH$ and $H_2O_2$ with a pulsating voltage of 0 to $+2$ V for about 5 to 10 min. Subsequently a voltage of $+0.4$ to $-0.40$ V is applied to the electrode for 10 minutes in a 1M $KNO_3$ solution.

The thickness of the filament or the wire is in the range of from 0.1 to 15 micrometers, advantageously from 5 to 15 micrometers, especially in the range of 8 to 10 micrometers. Since the electrode is advantageously conically tapered at one end, the diameter of the electrode filament can amount to about 0.10 micrometers at the tip.

The thickness of the insulating layer is in the range from 1.0 to 3.0 micrometers, advantageously in the range of 1.5 to 2.0 micrometers. It was found that a cross-linked insulating layer with a layer thickness in this range provides the desired insulating effect.

The end of the electrode is formed like a disk, as is illustrated in FIG. 1. The thickness of the insulating layer can be equal to or smaller than the diameter of the filament at the tip of the electrode.

So that the electroactive surface of the ultramicroelectrode can be modified, e.g. by coating or a metal or an ion selective layer and so that a satisfactory electrical contact of the ultramicroelectrode is possible, the end regions are free of insulating layers. One such end region of the ultramicroelectrode free of the insulating layer can be attained when one dissolves away the polymer layer chemically again after the electrochemical deposition of it. Here the fact that the uncross-linked linear polymer is not soluble in the aqueous system but is in different organic solvents is used. Alternatively it is also possible to free the tip of the ultramicroelectrode after the cross-linking mechanically so the electrode filament is exposed there. The tip of the electrode can be cutaway.

The electrode shown in FIG. 2 can be made, in which the tip region 3 of the electrode 3 prior to application of the insulating layer is covered with a galvanic resist or a metal. The galvanic resist protects the region 3 during the electrochemical polymerization prior to deposition of the polymer layers. After the insulating layer 2 was applied, the galvanic resist is again etched away chemically. Commercially obtainable galvanic resists and etching means can be used. The regions 3 and 4 can be covered especially accurately, when a currentless chemical or electrochemical deposition is performed e.g. by copper or nickel. These metal can be etched again chemically after they have fulfilled their protective function.

To avoid transfer resistance in transmission of the measured signal, e.g. with a carbon filament, the end portion is coated in FIG. 2A with metal. Thus the metals used already for masks, e.g. copper or nickel, after coating with polymer and its cross-linking remain on the filament or additional Noble metals are applied in corrosive media using the electrode. Also gold- or silver-filled conductive adhesive can be used for metallizing.

The tip of the ultramicroelectrode free of insulating material, which can be, shaped both like a disk(ee FIG. 1A) or as a cylinder(see FIG. 2A), is metallized electrochemically, e.g. with Mercury, so that the electrode may be used for analytical measurements, e.g. for inverse voltammetry.

Figure 3A:
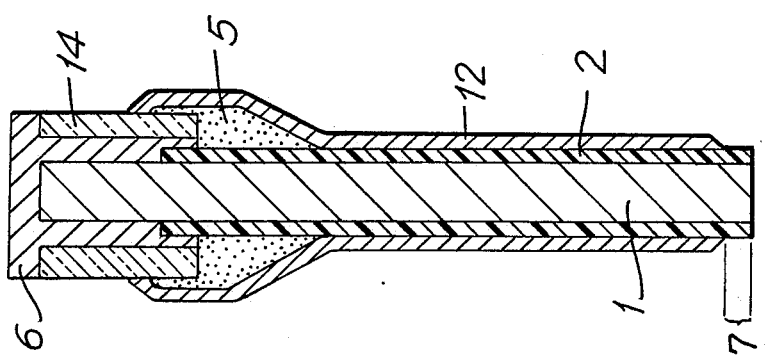
FIG. 3A is a longitudinal cross sectional view of an additional embodiment of an ultramicroelectrode.

The bipolar ultramicroelectrode shown in FIG. 3A is made when a metal layer is applied to the cross-linked polymer layer either chemically currentlessly and subsequently electrochemically or with physical methods, e.g. by vapor deposition of a metal layer, advantageously noble metals such as platinum, palladium or gold. The layer thickness of the metal layer amounts to from 0.2 to 5 micrometers, advantageously 0.5 to 1 micrometer.

The chemical metallizing can be performed by a process for currentless copper deposition on nonconducting material which is available commercially. Since the outer metal layer is connected as a counterelectrode to the inner disk-or cylindrical ultramicroelectrode(1), a sufficiently large region can be kept free of metal between the working electrode(inner conductor, e.g. carbon filament) and a counterelectrode(outer conductor—metal) to avoid short circuits. The spacing between the working and counterelectrodes is chosen depending on the conductivity of the electrolyte, and is advantageously less than 2 mm.

Furthermore the metal-free insulated region is either masked prior to the chemical copperization or the already deposited copper is etched away chemically or electrochemically. A suitable etching resist or galvanic resist obtained commercially can be used for masking. Subsequently the remaining copper layer can be reinforced electrochemically with Noble metals such as gold, platinum or palladium.

When the metallizing of the isolated polymer layers occurs with the help of a physical process, the above-mentioned region between the working electrode and counterelectrode to be kept free of metal can be coated with either a mask mechanically or with a layer(etching resist or galvanic resist), which can be dissolved away chemically. Also the chemical or electrochemical dissolution of the applied noble metal layer is possible.

To improve the adhesion of the noble metal layer on the polymer a metal intermediate layer, e.g. a Ti/W alloy, chromium or vanadium, are used. The choice of intermediate layers depends on the noble metal used.

The shielded ultramicroelectrode shown in FIG. 3B is made like the ultramicroelectrode shown schematically in FIG. 3A, except that the lower portion is kept free of metal to avoid short circuits. The spacing between the working and the counter electrode is dependent on the conductivity of the electrolyte, spacing is less than about 2 mm.

Moreover the metal-free insulated region is either masked before chemical copper deposition or the already deposited copper is etched away chemically currentlessly or electrochemically. For masking a suitable commercially obtainable galvanic resist or etching resist is used. Subsequently the residual copper layer is reinforced electrochemically with a noble metal such as gold, platinum or palladium.

When the metallizing of the insulated polymer layer occurs with the help of a physical process, the abovementioned region kept free of metal between the working electrode and the counterelectrode is either covered mechanically prior to masking or coated with an inert layer(etching resist or galvanic resist), which is subsequently dissolved chemically. Also the chemical or electrochemical dissolution of the applied noble metal layer is possible.

To improve the adhesion of the noble metal layer on the polymer a metallic intermediate layer such as a Ti/W-alloy, chromium or vanadium is used. The choice of the intermediate layer depends on the noble metal used.

The shielded ultramicroelectrode shown in FIG. 3B is made like the ultramicroelectrode formed schematically in FIG. 3A in which the lower end portion is free of metal. Additionally a polymer layer is deposited on the metal layer 12 and subsequently cross-linked to an insulator. The metal layer 12 is grounded and acts as a shield. The shield is advantageously used with an ultramicroelectrode with very small electroactive surface, with current flow in the picoampere range and for measurements in the M Hz region.

The illustrated ultramicroelectrodes are useable specially in biochemical and medical regions, for example as amperometric or potentiometric sensors or as stimulation electrodes and/or as electrodes for quantitative analysis, particularly for inverse Voltammetry.

According to an advantageous embodiment of our invention the ultramicroelectrodes can be used as potentiometric microsensors. One of the regions free of an insulating layer is provided with an ion selective layer, which contains an ion selective material. Suitable ion selective materials are for example salts, weakly soluble metals or ion-exchange resins, crown ethers, complex building agents and the like, which are embedded in the matrix of a polymer(e.g. PVC, silicone rubber and the like). Ion selective layers have membrane functions and allow only substances to be determined which are detected over the conductor. The ion selective layer may not be fully insulated.

According to an advantageous embodiment of our invention the ion-selective layer contains as a matrix a copolymer made from substituted phenol-, thiophenol- and/or aniline-containing monomers with unsaturated aliphatic groups in at least some of their ortho-positions with at least one noncross-linkable OH, $NH_2$— or SH-containing aromatic comonomers. The copolymer is formed by electrochemical deposition and subsequent cross-linking, as previously done with the insulating layer. The ion selective material can be embedded in the copolymer layer by impregnation or absorption as a component of the electrolytic solution or after during the electrochemical deposition or after the cross-linking. So that the matrix material has the membrane properties desired for an ion-selective layer, the electrochemical deposition is formed in the presence of a noncross-linkable OH—, NH— or SH-containing aromatic comonomer. A phenol, a thiophenol or an aniline with a saturated alkyl group with one to ten carbon atoms in the ortho-position is a suitable comonomer. The alkyl group has advantageously one to five carbon atoms. o-Cresol or ethyl phenol is a suitable comonomer.

The noncross-linkable comonomer used is at least 40 Mol % of the total monomer concentration, especially 50 to 80 Mol %. The proportion of the monomer with unsaturated aliphatic groups amounts to appropriately 60 Mol % or less, particularly 20 to 50 Mol %.

The proportion of ion selective materials in the layer amounts to appropriately 0.5 to 5 Gew-% relative to the matrix material. The thickness of the ion selective layer is 1 to 3 micrometers, advantageously 1.5 to 2 micrometers.

Our invention is illustrated in more detail by the following example:

EXAMPLE

An ultramicroelectrode is made according to the embodiment shown in FIG. 1. A carbon filament with a diameter of 8 micrometers, with a conically tapered tip or end was coated anodically in the following electrolytic solution:

| | |
|---|---|
| 0.23 Mol/l | 2-Allyl phenol |
| 0.40 Mol/l | Allyl amine or ammonia |
| 0.20 Mol/l | Cellosolve (Ethylene glycol monobutyl ether) |

Dissolved in Methanol and Water 1:1 (volume proportions)

The electrochemical polymerization was performed at a constant potential of 4 V at room temperature for 30 minutes. Subsequently the polymer layer is heated in an oven at 150° C., whereby a cross-linking of the deposited polymer layer occurs. The insulating layer formed has a layer thickness of 1.5 micrometers, which is sufficient for insulation purposes. The measured direct current resistance amounts to 2 Megohms. The breakdown voltage in a 1M KCl solution is larger than one million volts per centimeter. The capacitance of the insulating layer amounts to about 1 pF(picofarad). Because of the reduced double layer capacitance the signal/noise ratio during the measurement is very low, which allows a rapid single reception.

It will be understood that each of the elements described above, or two or more together, may also find a useful application in other types of constructions differing from the types described above.

While the invention has been illustrated and described as embodied in an ultramicroelectrode, a process for making it and a process for using it, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of this invention.

What is claimed as new and desired to be protected by Letters Patent is set forth in the appended claims:

1. In an electrode having a wire made of noble metal and/or carbon and an insulating layer applied thereon, the improvement wherein said insulating layer is made from a compound selected from the group consisting of substituted poly(1,4-phenylene) ethers, poly(1,4-phenylene) thioethers and poly(1,4-aniline)s, whose plurality of phenyl groups are cross-linked at their ortho-positions by alkylene groups with from two to ten carbon atoms.

2. The improvement defined in claim 1 wherein the thickness of said insulating layer amounts to from 1.0 to 3.0 micrometers and said wire has a diameter of from 0.10 to 15 micrometers.

3. The improvement defined in claim 1 wherein said wire is shaped like a disk having one end, which is free of said insulating layer.

4. The improvement defined in claim 1 wherein said wire has both end regions which are free of said insulating layer.

5. The improvement defined in claim 1 further comprising a metal electrode applied to a surface of said insulating layer.

6. The improvement defined in claim 5 further comprising another insulating layer applied to said metal electrode.

7. The improvement defined in claim 1 wherein said wire has one end region, which is free of said insulating layer and further comprising metal applied to said end region.

8. The improvement defined in claim 7 wherein said metal is also applied to another end region of said wire.

9. The improvement defined in claim 1 wherein said wire has a portion which is free of said insulating layer and provided with an ion selective layer.

10. The improvement defined in claim 9 wherein said ion selective layer contains as a matrix a copolymer selected from the group consisting of phenol-, thiophenol-, aniline-containing monomers and their combinations with an unsaturated group in an ortho-position with another comonomer selected from another group consisting of noncross-linkable OH—, $NH_2$— or SH-containing aromatic comonomers, which have a saturated aliphatic group in another ortho-position with 1 to 10 carbon atoms.

11. A process for making an electrode comprising a wire made of a noble metal or carbon and an insulating layer thereon comprising the steps of:
 a. depositing a polymer layer anodically on said wire made of said noble metal and/or carbon by electrochemical polymerization of monomers selected from the group consisting of phenol-, thiophenol-, aniline-containing monomers and their combinations, which contain in an ortho-position unsaturated aliphatic groups with 2 to 10 carbon atoms, from an electrolytic bath having an alkaline medium, which contains an amine and an adhesion promoting agent; and
 b. cross-linking said polymer layer to form said insulating layer.

12. The improvement defined in claim 11 wherein said alkaline medium contains an amine.

13. The improvement defined in claim 11 wherein said alkaline medium contains a primary amine with another aliphatic group.

14. The improvement defined in claim 11 wherein said alkaline medium contains an aqueous ammoniacal solution.

15. The improvement defined in claim 11 wherein said alkaline medium contains a mixture of an amine and an aqueous ammoniacal medium.

16. The improvement defined in claim 11 further comprising heating to effect said cross-linking.

17. The improvement defined in claim 11 further comprising irradiating to effect said cross-linking.

18. The improvement defined in claim 11 further comprising cleaning chemically for removal of a passive layer prior to said depositing.

19. The improvement defined in claim 11 further comprising cleaning electrochemically for removal of a passive layer prior to said depositing.

20. The improvement defined in claim 11 further comprising dissolving away said polymer layer chemically in an end region after said depositing of said polymer layer.

21. The improvement defined in claim 11 further comprising metallizing an end region of said wire prior to said depositing.

22. The improvement defined in claim 11 further comprising metallizing both end regions of said wire prior to said depositing.

23. The improvement defined in claim 11 further comprising mechanically opening a tip of said wire after said cross-linking of said polymer layer to said insulating layer so that said wire is exposed.

24. The improvement defined in claim 11 further comprising metallizing said insulating layer to form a metal layer with a metallizing process selected from the group consisting of a physical metallizing process, a currentless chemical metallizing process and an electrochemical metallizing process after said depositing of said polymer layer and subsequently performing said cross-linking.

25. The improvement defined in claim 24 further comprising removing a portion of said insulating layer, which is within 2 mm of an electroactive end region of said wire, and masking said portion prior to said metallizing.

26. The improvement defined in claim 24 further comprising removing a portion of said insulating layer, which is within 2 mm of an electroactive end region of said wire, and after said metallizing freeing said portion of metal by a method selected from the group consisting of a currentless chemical method and an electrochemical method.

27. The improvement defined in claim 24 further comprising applying again an additional polymer layer to said metal layer and cross-linking.

28. The improvement defined in claim 11 further comprising applying an ion selective layer to an end region of said wire free of said insulating layer.

29. The improvement defined in claim 28 further comprising forming and subsequently cross-linking a matrix for said ion selective layer having a copolymer layer made from the group consisting of phenol-, thiophenol- and aniline-containing monomers, which have an unsaturated aliphatic group in an ortho-position, with at least one other comonomer selected from another group consisting of noncross-linkable OH—, $NH_2$— and SH-containing aromatic monomers by electrochemical deposition and embedding a plurality of ion selective components therein during said depositing.

30. The improvement defined in claim 29 wherein the total amount of said monomers contains at least 40 Mol % of said noncross-linkable monomers.

31. The improvement defined in claim 28 further comprising forming and cross-linking a matrix for said ion selective layer having a copolymer layer made from a comonomer selected from the group consisting of phenol-, thiophenol-, aniline-containing monomers and their combinations, which have an unsaturated aliphatic group in an ortho-position, with at least one other comonomer selected from another group consisting of a noncross-linkable OH—, $NH_2$— and SH-containing aromatic monomers by electrochemical deposition and embedding a plurality of ion selective components after said cross-linking of said copolymer layer.

32. The improvement defined in claim 30 wherein the total amount of said monomers contains at least 40 Mol % of said noncross-linkable monomers.

33. The improvement defined in claim 11 wherein said insulating layer is chemically inert.

* * * * *